United States Patent [19]

Höpfl et al.

[11] Patent Number: 5,665,533

[45] Date of Patent: Sep. 9, 1997

[54] SKIN TEST TO HUMAN PAPILLOMAVIRUS TYPE 16

[75] Inventors: Reinhard Höpfl, Innsbruck, Austria; Ingrid Jochmus-Kudielka, Washington, D.C.; Lutz Gissmann, Wiesloch, Germany

[73] Assignee: Behringwerke Aktiengesellschaft, Marburg, Germany

[21] Appl. No.: 408,175

[22] Filed: Mar. 22, 1995

Related U.S. Application Data

[63] Continuation of Ser. No. 94,590, Jul. 21, 1993, abandoned, which is a continuation of Ser. No. 975,969, Nov. 13, 1992, abandoned, which is a continuation of Ser. No. 729,317, Jul. 15, 1991, abandoned.

[30] Foreign Application Priority Data

May 17, 1991 [DE] Germany ............................ 9106105 U

[51] Int. Cl.⁶ .............................. C12Q 1/70; C12N 15/37; C12N 7/00; A61K 39/12
[52] U.S. Cl. ........................... 435/5; 435/235.1; 436/63; 530/350; 530/403; 536/23.72
[58] Field of Search ...................... 435/5, 235.1; 436/63; 530/350, 403; 536/23.72

[56] References Cited

PUBLICATIONS

Zhor et al, Virology 181(1):203–210, 1991.
Zhor et al, J. Gen. Vir. 71(9):2185–90, 1990.
Viac et al, Br. J. Vener. Dis. 54(3):172–5, 1978.
Strang et al, J. Gen. Virol. 71(2):423–31, 1990.
Dordick et al, Lancet 337, Feb. 9, 1991, pp. 373–374.
L. Banks et al "Expression of HPV–6 & 16 Capsid Proteins in Bacteria and Their Antigenic Characteristics" J. Gen. Vir. 68. 1987, pp. 3081–3089.
D. Huw Davies et al "Definition of murine T helper cell determinants in the major cupsid protein of human papillomavirus type 16" J. Gen. Vir. 71. 1990. pp. 2691–2698.
I. M Roitt et al "Immunology" Harper & Row, NY NY. 1989 p. 22.4.
Martin Muller et al. "Identification of seroreactive regions of the human papillomavirus type 16 proteins E4, E6, E7 and L1" J. Gen. Vir. 71. 1990. pp. 2709–2717.

Primary Examiner—Mary E. Mosher
Assistant Examiner—Michael Chen
Attorney, Agent, or Firm—Finnegan, Henderson, Farabow, Garrett & Dunner, L.L.P.

[57] ABSTRACT

The invention relates to a skin test to human papillomavirus (HPV) type 16.

6 Claims, No Drawings

SKIN TEST TO HUMAN PAPILLOMAVIRUS TYPE 16

This application is a continuation of application Ser. No. 08/094,590 filed Jul. 21, 1993, now abandoned, which is a continuation of application Ser. No. 07/975,969 filed Nov. 13, 1992, abandoned, which is a continuation of application Ser. No. 07/729,317 filed Jul. 15, 1991, abandoned.

The invention relates to a skin test to human papillomavirus (HPV) type 16.

The HPV16 is a type of the human papillomavirus which has been first described in Proc. Natl. Acad. Sci., USA 80, 3813–3815 (1983).

The DNA-sequence and the genome organization of HPV16 have been published in Seedorf et al. Virology 145, 181–185 (1985).

HPV16 is closely related not only to benign lesions of the anogenital tract but also to malignant cancer of the uterine cervix, penis and vulva. In addition HPV16 can also be found in genital scrapes obtained from clinically asymptomatic individuals. Little is known about the immune response to infections by HPV16 and papillomaviruses in general.

Some seroreactive epitopes within the proteins E4, E6, E7 and L1 of HPV were disclosed in Müller, M. (990), J. Gen. Virol. 71, 2709–2717

However, efficient screening tests for active and latent high-risk human papilloma virus (HPV)—infections are not available at present. Classical intracutaneous tests using viral fusion proteins have not as yet been employed for this purpose; such tests may potentially allow to determine cell mediated immune responses (Schreier A. A. et al. Prospects for Human Papillomavirus Vaccines and Immunotherapies. J. Natl. Cancer Inst. 1988, 80, 896–899) in vivo against viral proteins and thus provide insight into epidemiology and course of HPV infection.

It has now been surprisingly discovered that positive reactions were observed to protein L1 of HPV 16 but not to protein E4 of HPV 16 in a skin test.

The present invention, therefore, concerns:

1. Diagnostic kit for detecting human papilloma virus infections, containing an efficient amount of protein L1 of human papilloma virus 16 or immunological parts thereof.
2. Diagnostic kit for detecting human papilloma virus infections in patients with cervical intraepithelial neoplasia containing an efficient amount of protein L1 of human papilloma virus 16 or immunological-parts thereof.

In order to develop a diagnostic kit and to perform a specific skin test the HPV16 open reading frames E4 and L1 (Seedorf et al. (1987), EMBO J., 6, 139–144), particularly the N-terminal part L112 and the C-terminal part, L1232 were cloned, expressed and the corresponding proteins of E4, L1 or parts thereof were isolated using general recombinant techniques, suitable expression vectors and purification methods well known in the art. Control proteins were identically prepared from the host cell containing the expression vector without viral insert. In general, the test procedure included intracutaneous (i.c.) injection of an efficient amount of protein L1 of HPV16 of about 9–25 µg, preferable about 9–15 µg, particularly about 10 µg of e.g. about 0.03–0.05 ml of each protein solution (to protein content about 300–500 µg/ml) along with injections of control solutions.

The tests were preferably carried out in patients with cervical intraepithelial neoplasias (CIN). Optionally, positive skin tests were biopsied and subjected e.g. to routine histopathology, immunocytochemistry or immunofluorescence. Blood samples were additionally used for serological assays, although biopsy and the serological assays are not necessary to perform an efficient and specific skin test for HPV16.

The results show that HPV L1 protein is useful in a sensitive and specific skin test in order to screen for CIN. In comparison, antibodies against E4 can only be detected in up to 42.6% of patients with CIN (Jochmus-Kudielka, I. et al. "Antibodies against the human papillomavirus type 16 early proteins in human sera: correlation of anti-E7 reactivity with cervical cancer." J. Natl. Cancer Inst. 1989, 81, 1698–1704).

The following non-limiting example illustrates the invention.

The HPV 6open reading frames E4 and L1 (N-terminal part=L112 C-terminal part=L1232) were cloned into pEX/ vectors, expressed in $E.\ coli$ C600/537 as MS2-polymerase fusion proteins (Jochmus-Kudielka, I., Gissmann, L. (1990): Expression of human papillomavirus type 16 proteins in Escherichia coli and their use as antigens in serological tests. In: Recombinant systems in protein expression. Alitalo, K. K., Hutala, M. L., Knowlers, J., Vaheri, A., eds. Amsterdam: Elsevier Science Publishers B. V. 87–93), prepared by extraction with 7M Urea and purified by gel extraction. Protein solutions (appr. protein content 300 µg/ml) were sterilized and stored in aliquots. Control proteins were identically prepared from extracts-of bacteria containing the pEX expression vector without viral insert. Skin tests were performed in volunteers, after permission by the local ethical committee was obtained.

The test procedure included i.c. injection of 0.03 ml of each protein solution along with injections of control solutions and testing of recall antigens (Mérieux multitest). The tests were carried out in a) seven female patients with cervical intraepithelial neoplasias (CIN) of at least 1 year duration and positive filter hybridisation for HPV16/18—one patient also HPV16 positive by polymerase chain reaction (PCR) —but negative for 6/11/31/33/35 (ViraType$^R$, GIBCO/BRL) and b) ten controls with no history of and no clinical evidence for genitoanal warts (four male physicians and six females; the latter exhibited no cervical cytological abnormality, had negative hybridisation tests for all HPV detailed above and, additionally, were negative for HPV16 by the PCR).

Positive skin test sites were biopsied at days 2, 3, 7 or 8 and subjected to routine histopathology, immunocytochemistry and immunofluorescence. Blood samples of volunteers were drawn immediately before injections and used for serological assays.

All individuals tested reacted to the Mérieux multitest in the range of normal. None of the control individuals reacted to HPV16 fusion protein. In contrast, five of seven patients with CIN exhibited clearly positive reactions to L1232 (p=0.0034, Fisher exact test (Armitage, P., Statistical methods in medical research, Blackwell, Oxford 1971), two tailed probability). Three of these and one additional patient reacted to L112 (p=0.0147), one patient reacted to neither protein fragment. No reactivity was observed to E4or the control proteins.

5 of 9 positive reactions took a biphasic course with an early in addition to the late response. Early responses (skin colored wheals of up to 5 mm diameter) arose 24 hours after injection, reached a maximum size after one week and lasted more than 3 weeks. Titration of L1/1/2 antigen was performed in one patient and resulted in discernible positive reactions (late) up to a 1:100 dilution of the protein preparation (=0.01 µg fusion protein). Histopathology of early response biopsies showed an Arthus-like reaction with neutrophilic vasculitis and vascular IgM and C3 deposits. Late response biopsies displayed dense lymphocytic infiltrates which were similar to the tuberculin reaction (Kuramoto, Y. & Tagami, H. Histopathologic pattern analysis of human intracutaneus tuberculin reaction. Am. J. Dermatopathol. 1989, 11, 329–337) and reminiscent of the infiltrate seen in spontaneously regressing plane warts (Iwatsuki, K. et al. Plane warts under spontaneus regression. Arch. Dermatol. 1986, 122, 655–659) (predominantly UCHL 1 positive memory cells, natural killer cells virtually absent, a few scattered giant cells).

None of five control individuals had anti HPV16 E4 antibodies, whereas in four of six CIN patients, including the one with a negative skin test, sero-reactivity to the E4 protein was detectable.

We claim:

1. A method for detecting a cell-mediated immune response to human papilloma virus comprising
    a. performing an intracutaneous skin test with an effective amount of protein L1 of human papilloma virus 16 or immunologically active parts thereof, and a means for administering said protein into the skin with a pharmaceutically acceptable diluent, and
    b. observing reactivity to the protein on the skin at the administration site.

2. A method for detecting a cell-mediated immune response to human papilloma virus in patients with cervical intraepithelial neoplasia comprising
    a. performing an intracutaneous skin test with an effective amount of protein L1 of human papilloma virus 16 or immunologically active pads thereof, and a means for administering said protein into the skin with a pharmaceutically acceptable diluent, and
    b. observing reactivity to the protein on the skin at the administration site.

3. The method according to claim 1 wherein said immunologically active part is L112.

4. The method according to claim 1 wherein said immunologically active part is L1232.

5. The method according to claim 2 wherein said immunologically active part is L112.

6. The method according to claim 2 wherein said immunologically active part is L1232.

* * * * *